United States Patent
Crampton

(10) Patent No.: US 8,524,926 B2
(45) Date of Patent: Sep. 3, 2013

(54) EPOXIDATION OF AN OLEFIN

(75) Inventor: Hannah L. Crampton, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/509,664

(22) PCT Filed: Nov. 12, 2010

(86) PCT No.: PCT/US2010/002965
§ 371 (c)(1),
(2), (4) Date: May 14, 2012

(87) PCT Pub. No.: WO2011/062608
PCT Pub. Date: May 26, 2011

(65) Prior Publication Data
US 2012/0316353 A1 Dec. 13, 2012

Related U.S. Application Data

(60) Provisional application No. 61/281,546, filed on Nov. 19, 2009.

(51) Int. Cl.
*C07D 301/12* (2006.01)

(52) U.S. Cl.
USPC ...................................................... 549/531

(58) Field of Classification Search
USPC ...................................................... 549/531
See application file for complete search history.

(56) References Cited

U.S. PATENT DOCUMENTS

| | | |
|---|---|---|
| 6,300,506 B1 | 10/2001 | Paparatto et al. |
| 6,372,924 B2 | 4/2002 | Thiele |
| 6,429,322 B1 | 8/2002 | Catinat et al. |
| 6,673,950 B1 | 1/2004 | Teles et al. |
| 2006/0041150 A1 | 2/2006 | Catinat et al. |

FOREIGN PATENT DOCUMENTS

| | | |
|---|---|---|
| CN | 1329100 | 10/2008 |
| EP | 0230949 | 8/1987 |
| EP | 1085017 | 3/2001 |
| EP | 1403219 | 3/2004 |
| EP | 1403259 | 3/2004 |
| WO | 2004048353 | 6/2004 |
| WO | 2005063619 | 7/2005 |

OTHER PUBLICATIONS

International Search Report and Written Opinion from related PCT application PCT/US2010002965 dated Jun. 1, 2011, 14 pages.
Rao, et al. "1,5,7-Triazabicyclo[4.4.0]dec-5-ene immobilized in MCM-41: A Strongly Basic Porous Catalyst", Angewandte Chemie, International Edition in English, vol. 36, No. 23, 1997, 2661-2663. (XP002636500).

(Continued)

*Primary Examiner* — Taylor Victor Oh
(74) *Attorney, Agent, or Firm* — Brooks, Cameron & Huebsch, PLLC

(57) ABSTRACT

The present invention provides one or more embodiments of a process for the epoxidation of an olefin. For the embodiments, the process includes reacting the olefin, with the proviso that the olefin is not propylene, with a hydrogen peroxide solution at a predetermined pH in the presence of a catalyst and a solvent at a predetermined reaction temperature. The pH of the hydrogen peroxide solution is adjusted to the predetermined pH by contacting the hydrogen peroxide solution with a supported base to remove acidic species from the hydrogen peroxide solution.

9 Claims, 1 Drawing Sheet

(56) References Cited

OTHER PUBLICATIONS

Fraile, et al. "Basic Solids in the Oxidation of Organic Compounds", Catalysis Today, No. 57, 2000, 3-16. (XP002636501).

Gonzalez, et al. "Immobilization of Methyltrioxorhenium onto tertiary amine and pyridine N-Oxide resins", Reactive & Fundamental Polymers, No. 63, 2005, 169-181 (XP005146688).

Grivani, et al. "A readily prepared, highly reusable and active polymer-supported molybdenum carbonyl Schiff base complex as epoxidation catalyst", Inorganic Chemistry Communications, vol. 10, No. 8, 2007, 914-917. (XP022164836).

Xiwen, et al. "Epoixidation of propylene with dilute H2O2 over titanium silicalite containing trace aluminum", Catalysis Letters, 2002, 81, 125-130.

Shetti, et al. "Enhancement of chemoselectivity in epoxidation reactions over TS-1 catalysts by alkali and alkaline earth metal ions", Journal of Molecular Catalysis A: Chemical, 210, 2004, 171-178.

Wang, et al, "Synthesis of titanium silicate (TS-1) from the TPABr system and its catalytic properties of epoxidation of propylene", Catalysis Today, 74, 2002, 65-75.

Li, et al. "Epoxidation of Allyl Chloride to Epichlorohydrin by a Reversible Supported Catalyst with H2O2 Under Solvent-Free Conditions", Organic Process Research & Development, 10, 2006, 876-880.

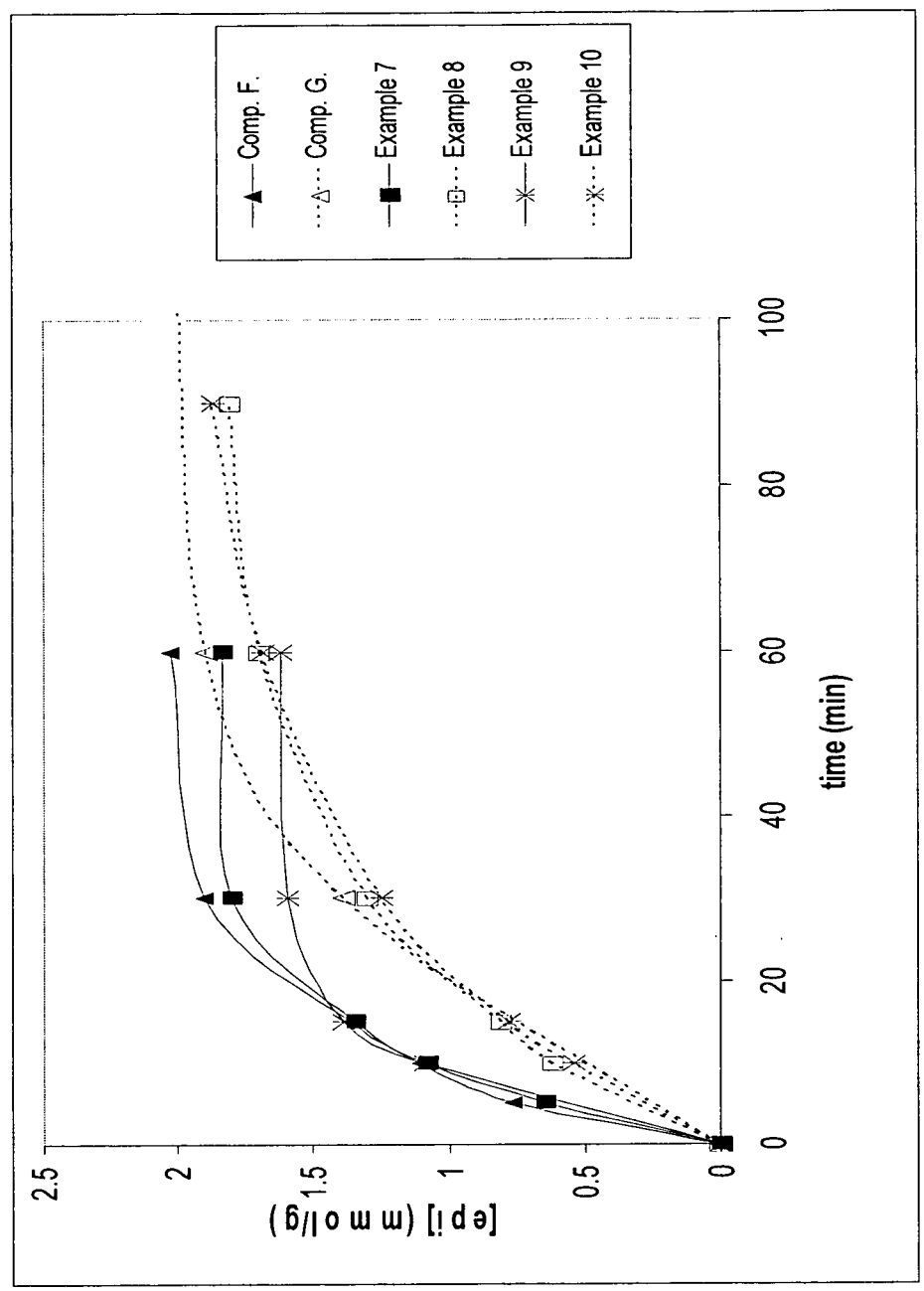

EPOXIDATION OF AN OLEFIN

This application is a National Stage application under 35 U.S.C. 371 of PCT/US2010/002965, filed on Nov. 12, 2010 and published as WO2011/062608 A2 on May 26, 2011, which claims the benefit of U.S. Provisional Application Ser. No. 61/281,546 filed Nov. 19, 2009, the entire contents of which are incorporated herein by reference in its entirety.

FIELD OF INVENTION

This invention relates to a process for an epoxidation of an olefin to produce an epoxide.

BACKGROUND

Epoxides are produced by a variety of techniques. One commercial technique for the production of epoxides includes reacting an olefin with hydrogen peroxide and one or more catalysts in a protic medium. The epoxidation of olefins in a protic medium, however, can decrease the selectivity of the epoxidation reaction. In addition to a decrease in selectivity, the amount of by-products formed during the epoxidation can increase as the epoxide reacts with the protic medium and as the epoxide oligomerizes and/or polymerizes. This decrease in selectivity also increases the costs of production due to a lower yield of epoxides and the steps required to separate the by-products from the epoxide.

As such, efforts have been made to increase the selectivity of the epoxidation process. Such efforts include using pretreated catalysts and homogeneous organic or inorganic compounds to change the pH of the reaction mixture. However, while the selectivity of the epoxidation reaction may increase in these previous approaches, the hydrogen peroxide utilization, hydrogen peroxide conversion and the lifetime of the catalyst can decrease simultaneously. These drawbacks decrease the efficiency of the production by yielding less epoxide for the amount of materials used.

SUMMARY

The present invention provides one or more embodiments of a process for an epoxidation of an olefin. For the embodiments, the epoxidation of the olefin includes reacting the olefin, with the proviso that the olefin is not propylene, with a hydrogen peroxide solution at a predetermined pH in the presence of a catalyst and a solvent at a predetermined reaction temperature. The pH of the hydrogen peroxide solution is adjusted to the predetermined pH by contacting the hydrogen peroxide solution with a supported base to remove acidic species from the hydrogen peroxide solution. For the embodiments, a selectivity of the epoxidation of the olefin is increased without decreasing a hydrogen peroxide utilization or a hydrogen peroxide conversion as compared to an epoxidation of an olefin without the supported base to adjust the pH of the hydrogen peroxide solution to the predetermined pH. Additionally, the present invention provides an epoxide obtained by the process described herein.

Embodiments of the present invention also include a process for preparing epichlorohydrin. For the embodiments, the process for preparing epichlorohydrin includes reacting allyl chloride and a hydrogen peroxide solution at a predetermined pH, in the presence of a catalyst and a solvent. The pH of the hydrogen peroxide solution is adjusted to the predetermined pH by contacting the hydrogen peroxide solution with a supported base to remove acidic species from the hydrogen peroxide solution. For the embodiments, a selectivity of an epoxidation of allyl chloride is increased without decreasing a hydrogen peroxide utilization or a hydrogen peroxide conversion as compared to an epoxidation of allyl chloride without the supported base to adjust the pH of the hydrogen peroxide solution to the predetermined pH.

BRIEF DESCRIPTION OF THE DRAWINGS

FIG. 1 illustrates the amount of epichlorohydrin formed during an epoxidation of allyl chloride.

DETAILED DESCRIPTION

Definitions

"Epoxide" refers to a compound in which an oxygen atom is directly attached to two adjacent or non-adjacent carbon atoms of a carbon chain or ring system. Epichlorohydrin (epi) is an example of an epoxide and is formed from an epoxidation of allyl chloride.

"Selectivity" refers to the amount of epoxide formed relative the amount of epoxide formed plus all by-products.

"By-products" refers to all substances formed from an epoxidation of an olefin minus the epoxide. For example, for the epoxidation of allyl chloride, the by-products can include water, 1-chloro-3-methoxy-2-propanol (CMP), monochlorohydrin (MCH) and higher molecular weight by-products.

"Higher molecular weight by-products" refer to the by-products formed from the epoxidation of allyl chloride that elute after MCH during gas chromatography.

"Hydrogen peroxide conversion" refers to the amount of hydrogen peroxide that reacts during an epoxidation of an olefin relative the amount of hydrogen peroxide added to the reaction mixture.

"Hydrogen peroxide utilization" refers to the amount of hydrogen peroxide converted to an epoxide relative the amount of hydrogen peroxide that reacts during an epoxidation of an olefin.

"Supported base" refers to a non-soluble support bearing a basic functional group that has a neutral charge.

"Neutral charge" refers to a substance that does not have ions such that the substance has neither a positive nor negative electric charge.

"Stabilizer" refers to substances, and in particular acid(s), that include acidic species that are added to a hydrogen peroxide solution to reduce the rate of decomposition.

"Acidic species" refers to a substance that can donate a proton.

"Reaction mixture" refers to a mixture of an olefin, a hydrogen peroxide solution at a predetermined pH, a catalyst and a solvent. The reaction mixture can further include additional reagents including, but not limited to, a co-solvent that is more fully discussed herein.

For the embodiments, a process for an epoxidation of an olefin of the present invention (also referred to as "epoxidation process") includes reacting the olefin, with the proviso that the olefin is not propylene, with a hydrogen peroxide solution at a predetermined pH in the presence of a catalyst and a solvent at a predetermined reaction temperature. For the embodiments, a pH of the hydrogen peroxide solution is adjusted to the predetermined pH by contacting the hydrogen peroxide solution with a supported base to remove acidic species from the hydrogen peroxide solution. The process of the present invention increases a selectivity of the epoxidation of the olefin without decreasing a hydrogen peroxide utilization or a hydrogen peroxide conversion as compared to an epoxidation of an olefin without the use of the supported base to adjust the pH of the hydrogen peroxide solution to the predetermined pH.

For the embodiments, the epoxidation process includes reacting hydrogen peroxide with the olefin. The hydrogen peroxide is in an aqueous solution, referred to as a hydrogen peroxide solution, where the hydrogen peroxide in the hydrogen peroxide solution reacts with the olefin to produce an epoxide. The hydrogen peroxide solution can further contain other substances that may or may not participate in the epoxidation process that forms the epoxide. For example, acidic species can be present in the hydrogen peroxide solution and are discussed more fully herein.

For the embodiments, the olefin used in the process can be selected from the group consisting of linear and/or branched acyclic or cyclic aliphatic or aromatic olefins, including those which may contain multiple double bonds, with the proviso that the olefin is not propylene. For the embodiments, the olefin is preferably allyl chloride. Additional examples of the olefin include, but are not limited to, chloride-butadiene and other linear dialkenes, cyclohexene and other cyclic alkenes and dialkenes, substitute alkenes, such as halogenated alkenes, styrene, divinylbenzene, dicyclopentadiene, other aromatic alkenes and mixtures thereof. Moreover, butenes, pentenes, hexenes, octeneheptenes-1,1-tridecene, mesityl oxide, isoprene, cyclo-octane, cyclohexene or bicyclic compounds such as norbornenes or pinenes may also be used in the process.

For the embodiments, the amount of the olefin used in the reaction mixture can be within a range of from 10 weight percent (wt %) to 90 wt %, more preferably within a range of from 30 wt % to 70 wt %, and still more preferably within a range of from 40 wt % to 65 wt %, based on the total weight of the reaction mixture.

For the embodiments, the epoxidation process includes reacting the olefin with hydrogen peroxide, where the hydrogen peroxide is in the hydrogen peroxide solution. However, as one skilled in the art would appreciate, other organic and/or inorganic hydroperoxides may be used for the epoxidation of the olefin. Examples of other hydroperoxides that may be used include, but are not limited to, tert-butyl hydroperoxide, ethylbenzene hydroperoxide, acetyl peroxide, benzoyl peroxide, methyl ethyl ketone peroxide, cumene peroxide and combinations thereof. For the embodiments, the amount of the hydrogen peroxide solution used in the reaction mixture can be within a range of from 1 wt % to 35 wt %, more preferably within a range of from 1 wt % to 15 wt %, and still more preferably within a range of from 1 wt % to 7 wt %, based on the total weight of the reaction mixture.

Available sources of the hydrogen peroxide solution are produced by the hydrolysis of a persulphuric acid and, more commonly, the successive hydrogenation and oxidation of a substituted alkylanthroquinone in a suitable solvent system. Both methods produce a hydrogen peroxide solution that can contain high levels of impurities such as solids and transition metal ions that are introduced during the production of the hydrogen peroxide solution. Hydrogen peroxide solutions with even trace levels of impurities tend to decompose during storage and/or use. Therefore, stabilizers, which include acidic species, are added to the hydrogen peroxide solution to reduce and/or prevent decomposition. Examples of stabilizers can include phosphoric acid, nitric acid, tin, stannates, organic phosphates, or mixtures thereof.

For the embodiments, the epoxidation process includes adjusting a pH of the hydrogen peroxide solution to a predetermined pH prior to reacting the hydrogen peroxide solution with the olefin. The pH of the hydrogen peroxide solution is adjusted by contacting the hydrogen peroxide solution with a supported base. The supported base is selected from supported bases that have a predominantly neutral charge and do not participate in an ion exchange. In other words, the supported base does not donate an ion in exchange for another ion, but rather can either accept or donate ions, but not both. For the embodiments, the supported base can act like a "destabilizer" and reduce the acidic species and metals that may be present from the production of the hydrogen peroxide solution. The supported base can reduce acidic species present in the hydrogen peroxide solution by accepting ions, but does not donate ions in return. More specifically, the supported base can accept protons. By accepting the protons, the predominately neutral charge of the supported base will change to a positive charge while the pH of the hydrogen peroxide solution is adjusted to the predetermined pH.

For the embodiments, the amount of the supported base needed to adjust the pH of the hydrogen peroxide solution to the predetermined pH will depend on the amount of hydrogen peroxide solution being used in the reaction mixture and the predetermined pH value. Therefore, enough of the supported base is used until the predetermined pH of the hydrogen peroxide solution is achieved. For the embodiments, the predetermined pH can be within a range of from 1.0 to 9.0, more preferably within a range of from 3.0 to 7.0, still more preferably within a range of from 4.0 to 6.0, and most preferably within a range of from 5.0 to 5.5.

As discussed herein, the epoxidation process of the present invention can reduce the amount of by-products formed during the epoxidation of the olefin. The epoxidation of the olefin, such as allyl chloride, produces by-products that can include, water, 1-chloro-3-methoxy-2-propanol (CMP), -chloro-2,3-propanediol (MCH), and higher molecular weight by-products. These by-products can be formed by the stabilizers present in the hydrogen peroxide solution. For example, the acidic species in the stabilizers can catalyze a ring opening reaction during the formation of the epoxide. These ring opening reactions can produce the higher molecular weight by-products and a portion of the CMP and MCH by-products. Therefore, reducing the acidic species in the hydrogen peroxide solution limits the ring opening reaction and reduces the amount of by-products formed during the epoxidation. By limiting the ring opening reactions, the selectivity of the epoxidation of the olefin is increased and more epoxide is produced during the epoxidation. For the embodiments of the present invention, increasing the selectivity of is accomplished without decreasing the hydrogen peroxide utilization or the hydrogen peroxide conversion as compared to an epoxidation of an olefin without the supported base to adjust the pH of the hydrogen peroxide solution to the predetermined pH.

For the embodiments, the pH of the hydrogen peroxide solution is adjusted to the predetermined pH by contacting the hydrogen peroxide solution with the supported base. Contacting the hydrogen peroxide solution with the supported base can be performed in either a batch or continuous mode. For example, the hydrogen peroxide solution can be mixed with the supported base to form a heterogeneous solution or the hydrogen peroxide solution can be passed through a fixed-bed reactor that contains the supported base. For the embodiments, mixing the hydrogen peroxide solution with the supported base may be performed by known means for mixing, such as, but not limited to, stirring with an agitator or by inducing shear with a mixing element in a tubular reactor or loop reactor. Additionally, using combinations of the reactors to contact the hydrogen peroxide solution with the supported base may also be used.

For the embodiments, the epoxidation of the olefin is carried out in the presence of a catalyst. Additionally, more than one catalyst may be used in the epoxidation process. The catalyst used in the process can be selected from heterogeneous catalysts which comprise a porous oxide material such as zeolite. As appreciated, zeolites are solid containing silicas which have microporous crystalline ordered channels with a cage structure and pore openings. Along with microporous zeolites, mesoporous and macroporous zeolite type catalysts can also be used. For the embodiments, the catalyst is preferably selected from titanium-silicalites generally known as TS-1 having a MFI structure. It is also possible to use titanium-silicalites with a MEL or intermediate MFI/MEL structure and titanium-silicalites from beta zeolites containing titanium and having a BEA structure. Other titanium containing zeolite catalysts generally known as TS-2, TS-3, ZSM-48 and ZMS-12 can also be used.

For the embodiments, a portion or all of the titanium in the zeolite catalyst can be replaced by, but not limited to, boron, aluminum, iron, gallium, vanadium, zirconium, chromium, niobium or a mixture of two or more thereof. Additional examples of zeolites containing titanium, vanadium, chromium, niobium, and zirconium include, but are not limited to, BEA, MOR, TON, MTW, FER, CHA, ERI, RHO, GIS, BOG, NON, EMT, HEU, KFI, FAU, DDR, MTT, RUT, RTH, LTL, MAX, GME, NES, OFF, SGT, EUO, MFS, MWW and ITQ-4. It is also possible to use titanium-containing zeolites having the UTD-1, CIT-1 or CIT-5 structure in the process of the present invention. Furthermore, other heterogeneous and homogeneous catalysts may be used. Examples include, but are not limited to, soluble metal catalysts such as ligand-bound rhenium, tungsten, and manganese, along with the heterogenized forms of these.

For the embodiments, the catalyst can be used within a range of from 0.1 wt % to 30 wt %, more preferably within a range of from 0.1 wt % to 15 wt %, and still more preferably within a range of from 0.1 wt % to 5 wt %, based on the total weight of the reaction mixture.

Catalysts used in epoxidations will eventually deactivate. Once the catalyst deactivates, the deactivated catalyst can be separated and regenerated to be reused with a subsequent epoxidation process. The formation of by-products, and in particular the higher molecular weight by-products, can increase the rate of deactivation by plugging the pores of the catalyst. As provided herein, the epoxidation process of the present invention helps minimize the amount of by-products formed. Minimizing the by-products can reduce the rate at which the pores of the catalyst become plugged. Reducing the rate at which the pores of the catalyst become plugged can increase the lifetime of the catalyst as compared to an epoxidation of an olefin without using the supported base to adjust the pH of the hydrogen peroxide solution to a predetermined pH. For the embodiments, increasing the lifetime of the catalyst and reducing the frequency at which the catalyst needs to be separated and regenerated can reduce the cost and time associated with the epoxidation process.

For the embodiments, the epoxidation process is carried out in the presence of a solvent. The solvent can be selected from protic solvents. For example, alcohols, such as methanol, ethanol, isopropyl alcohol, tert-butyl alcohol and cyclohexanol, along with ketones, such as acetone, methyl ethyl ketone and acetophenone can be used. For the embodiments, the solvent is preferably methanol. The solvent can also be selected from ethers, hydro-alcohol mixtures, aliphatic and aromatic hydrocarbons, halogenated hydrocarbons, and esters. Mixtures of the various solvents may also be used. For the embodiments, the amount of the solvent in the reaction mixture can be within a range of from 3 wt % to 90 wt %, more preferably within a range of from 3 wt % to 50 wt %, and still more preferably within a range of from 3 wt % to 10 wt %, based on the total weight of the reaction mixture.

For the embodiments, the epoxidation process can be carried out in the presence of a co-solvent. The co-solvent can be selected from non-water soluble solvents that include, but are not limited to, linear and cyclic alkanes of $C_3$-$C_{18}$, halogenated hydrocarbons, deactivated aromatics, amides, solvents containing nitriles, alcohols, and halogenated alcohols or mixtures thereof. Examples of the co-solvent include, but are not limited to, carbon tetrachloride, propyl chloride, chloroform, dichloromethane, dichloroethane, hexane, octane, decalin, perfluorodecalin, mono or poly-chlorinated benzenes, mono- or poly-brominated benzenes, acetpheonone, benzonitrile, acetonitrile, trichlorotrifluoroethane, trichloroethanol, trifluoroethanol or mixtures thereof. For the embodiments, the co-solvent is preferably 1,2-dichlorobenzene. The co-solvent can be used within in a range of from 5 wt % to 70 wt %, more preferably within a range of from 10 wt % to 50 wt %, and still more preferably within a range of from 10 wt % to 30 wt %.

For the embodiments, the epoxidation process is carried out at a predetermined reaction temperature. For the embodiments, the predetermined reaction temperature can be within a range of from 0° C. to 100° C., more preferably within a range of from 10° C. to 80° C., and still more preferably within a range of from 40° C. to 60° C. In addition, the predetermined reaction temperature can remain at a constant temperature during the epoxidation of the olefin. For the embodiments, the epoxidation of the olefin is performed at 1 standard atmosphere (atm) (101.3 kilopascal), but other pressures may be used. Additionally, the pressure may be modified during the epoxidation.

For the embodiments, the epoxidation process can be carried out in either a continuous, a semi-continuous or in a batch process. The epoxidation process can also be carried out in at least one batch reactor or at least one continuous reactor, or in a combination of these. For example, the reactor may be selected from, but not limited to, one or more continuous stirred tank reactors, tubular reactors and combinations thereof. Additionally, the reactor may be selected from liquid-liquid contactors, such as a Karr Column.

For the embodiments, the hydrogen peroxide solution at the predetermined pH is added to a pre-reaction solution including the olefin, catalyst, solvent and co-solvent, if one is used, to form the reaction mixture. The hydrogen peroxide solution at the predetermined pH can be added to form the reaction mixture with or without the supported base. If desired, the supported base can be removed from the hydrogen peroxide solution by standard separating procedures, such as, but not limited to, vacuum filtration.

For the embodiments, a substantial portion of the resulting epoxide will form in an organic phase that can include unreacted olefin, the co-solvent, and a portion of the by-products. However, a portion of the resulting epoxide may reside in an aqueous phase that can include unreacted hydrogen peroxide, the solvent, and a portion of the by-products. Thus, the organic and aqueous phase can be separated from the supported base, if not previously removed, and the catalyst by conventional techniques for separation such as decantation, hydrocyclones, mechanically driven high gravity devices or combinations thereof. Additionally, the resulting epoxide can be separated and/or recovered from the organic phase and the aqueous phase using techniques, such as, but limited to, distillation.

EXAMPLES

The following examples are given to illustrate, but not limit, the scope of this invention.

Materials

Hydrogen peroxide solution (30 wt % aqueous solution), available from VWR.

Olefin, allyl chloride (99.4% purity), available from Freeport B6800 block allyl chloride plant. The olefin, allyl chloride, is also available from Sigma Aldrich, (Reagent Plus, 99%, CAS #107-05-1).

Solvent, methanol (99.8%, certified ACS, CAS #67-56-1), available from Fisher Scientific.

Co-solvent, 1,2-dichlorobenzene (Reagent Plus, 99%, CAS #95-50-1), available from Sigma Aldrich.

Catalyst, titanium-silicalite (TS-1, titanium content is approximately 2.1 wt %), available from Sijd-Chemie.

Supported base, poly-4-vinylpyridine (CAS #25232-41-1), available from Sigma Aldrich.

Supported base, Amberlyst® A-21 (free base, 20-5-mesh, CAS #9049-93-8), available from Sigma Aldrich.

Supported base, Lewatit® MP-62 (free base, 300-1000 micrometer (μm)), available from Sigma Aldrich.

Supported base, Dowex® MWA-1 (free base, 53-75 mesh, CAS #63993-97-9), available from Sigma Aldrich.

Ion exchange resin, Amberlyst® A-26 (hydroxide form, 16-45 mesh, CAS #39339-85-0, available from Sigma Aldrich.

Ion exchange resin, silica-supported trimethylpropyl ammonium carbonate (0.8 millimole per gram loading, 200-400 mesh), available from Sigma Aldrich.

Ion exchange resin, Reillex® HPQ (partially quaternized methyl chloride salt, 300-1000 μm particle size, CAS #125200-80-8), available from Sigma Aldrich, Homogeneous ionic base, sodium hydroxide (Reagent grade, ≧98%, CAS#1310-73-2), available from Sigma Aldrich.

Test Methods

Measurements of pH

The pH was measured on a Beckman model 45 pH meter using an Orion 8272BN combination electrode with 3M potassium chloride (KCl) filling solution. The Beckman was calibrated daily with pH=4 and pH=7 buffers.

Gas Chromatography

The gas chromatography (GC) was performed on an HP 6890 series G1530A GC with a JP 7682 series injector and flame ionization detector.

Titration

The amount of hydrogen peroxide was analyzed by iodometric titration using 0.01 normality (N) sodium thiosulfate. The hydrogen peroxide concentration was calculated as follows: parts per million (ppm) hydrogen peroxide=(ml) titrant used) (0.01 N) (17000)/g sample. Titrations were performed using a Mettler Toledo DL5x V2.3 titrator with a DM140 sensor.

Example 1

Epoxidation of Allyl Chloride Using Hydrogen Peroxide Solution with a Supported Base A pre-reaction solution was made by adding 52.3 wt % of allyl chloride, 5 wt % of methanol, 23.3 wt % of 1,2-dichlorobenzene and 1.4 wt % of the TS-1 catalyst to a 750 ml jacketed glass reactor with a stainless steel cooling coil, thermocouple, mechanical stirrer, additional funnel, nitrogen purge with gas scrubber, and reflux condenser/cold finger combination, where the weight percents are based on the total weight of the reaction mixture. The pre-reaction solution was heated to 25.5° C.

The hydrogen peroxide solution was stirred with enough Amberlyst® A-21 to adjust the pH of the hydrogen peroxide solution to a predetermined pH of 5.7. The amount of hydrogen peroxide solution stirred with the Amberlyst® A-21 was 18 wt % of the total reaction mixture. The mixture of the hydrogen peroxide solution and the Amberlyst® A-21 were added to the addition funnel. The hydrogen peroxide solution and Amberlyst® A-21 mixture were slowly added to the reactor containing the pre-reaction solution forming the reaction mixture. The reaction mixture was heated to the predetermined reaction temperature of 40° C. +/−0.5° C. for 60 minutes, while being stirred at 600 revolutions per minute (rpm). The contents of the reactor were collected from the reactor into two 250 milliliter (ml) centrifuge tubes and centrifuged at 3000 rpm at 0° C. for 30 minutes. The aqueous phase and the organic phase were decanted into a sepatory funnel. Both phases were analyzed with gas chromatography. The remaining hydrogen peroxide was determined by titration with sodium thiosulfate. The results of Example 1 and the following Examples 2-10 are illustrated in Table 1.

Example 2

Epoxidation of Allyl Chloride Using Hydrogen Peroxide Solution with a Supported Base The procedure in Example 1 was repeated, but with the following changes. The hydrogen peroxide solution was stirred with enough poly-4-vinylpyridine to adjust the pH of the hydrogen peroxide solution to a predetermined pH of 5.

Example 3

Epoxidation of Allyl Chloride Using Hydrogen Peroxide Solution with a Supported Base The procedure in Example 1 was repeated, but with the following changes. The hydrogen peroxide solution was stirred with enough Lewatit® MP-62 to adjust the pH of the hydrogen peroxide solution to a predetermined pH of 5.2.

Example 4

Epoxidation of Allyl Chloride Using Hydrogen Peroxide Solution with a Supported Base The procedure in Example 1 was repeated, but with the following changes. The hydrogen peroxide solution was stirred with enough Dowex® MWA-1 to adjust the pH of the hydrogen peroxide solution to a predetermined pH of 5.2.

Example 5

Epoxidation of Allyl Chloride Using Hydrogen Peroxide Solution with a Supported Base The procedure in Example 1 was repeated, but with the following changes. The hydrogen peroxide solution was stirred with enough poly-4-vinylpyridine to adjust the pH of the hydrogen peroxide solution to a predetermined pH of 4.5.

Example 6

Epoxidation of Allyl Chloride Using Hydrogen Peroxide Solution with a Supported Base The procedure in Example 1 was repeated, but with the following changes. The hydrogen peroxide solution was stirred with Amberlyst® A-21 to adjust the pH of the hydrogen peroxide solution to a predetermined pH of 4.6.

Example 7

Epoxidation of Allyl Chloride Using Hydrogen Peroxide Solution with a Supported Base The procedure in Example 1 was repeated, but with the following changes. The pH of the hydrogen peroxide solution was adjusted to a predetermined pH of 5.5. The Amberlyst® A-21 was separated from the hydrogen peroxide solution using vacuum filtration. The addition funnel was charged with the filtered hydrogen peroxide solution (i.e., the filtrate). The filtered hydrogen peroxide solution was then slowly added to the reactor containing the pre-reaction solution.

Example 8

Epoxidation of Allyl Chloride Using Hydrogen Peroxide Solution with a Supported Base and Catalyst Reuse The procedure in Example 7 was repeated, but with the following changes. Instead of using fresh TS-1 for the catalyst, the separated catalyst from Example 7 was reused. The pH of the hydrogen peroxide solution was adjusted to a predetermined pH of 5.6 before vacuum filtration.

Example 9

Epoxidation of Allyl Chloride Using Hydrogen Peroxide Solution with a Supported Base The procedure in Example 7 was repeated, but with the following changes. The hydrogen peroxide solution was stirred with enough poly-4-vinylpyridine to adjust the pH of the hydrogen peroxide solution to a predetermined pH of 5.6 before vacuum filtration.

Example 10

Epoxidation of Allyl Chloride Using Hydrogen Peroxide Solution with a Supported Base and Catalyst Reuse The procedure in Example 8 was repeated, but with the following changes. Instead of using frest TS-1 catalyst, the separated TS-1 catalyst from Example 9 was reused. The hydrogen peroxide solution was stirred with enough poly-4-vinylpyridine to adjust the pH of the hydrogen peroxide solution to a predetermined pH of 5.4 before vacuum filtration.

Comparative Examples

The following are comparative examples. Comparative Examples A-E adjust the pH of the hydrogen peroxide solution with ion exchange resins and homogeneous ionic bases. Comparative Examples F and G do not use any form of pH adjustment or control. The results of the comparative examples are illustrated in Table 2 and Table 3.

Comparative Example A

Epoxidation of Allyl Chloride Using Hydrogen Peroxide Solution with an Ion Exchange Resin The procedure from Example 1 was repeated, but with the following changes. The hydrogen peroxide solution was stirred with enough Amberlyst® A-26 to adjust the pH of the hydrogen peroxide solution to 5.5.

Comparative Example B:

Epoxidation of Allyl Chloride Using Hydrogen Peroxide Solution with an Ion Exchange Resin The procedure from Example 1 was repeated, but with the following changes. The hydrogen peroxide solution was stirred with enough silica-supported trimethylpropyl ammonium carbonate to adjust the pH of the hydrogen peroxide solution to 5.02.

Comparative Example C

Epoxidation of Allyl Chloride Using Hydrogen Peroxide Solution with an Ion Exchange Resin The procedure from Example 1 was repeated, but with the following changes. The hydrogen peroxide solution was stirred with enough Reillex® HPQ to adjust the pH of the hydrogen peroxide solution to 5.5.

Comparative Example D

Epoxidation of Allyl Chloride Using Hydrogen Peroxide Solution with a Homogeneous Ionic Base The procedure from Example 1 was repeated, but with the following changes. The hydrogen peroxide solution was mixed with enough sodium hydroxide aqueous solution to adjust the pH of the hydrogen peroxide solution to 5.6

Comparative Example E

Epoxidation of Allyl Chloride Using Hydrogen Peroxide Solution with a Homogeneous Ionic Base The procedure from Example 1 was repeated, but with the following changes. The hydrogen peroxide solution was mixed with enough sodium hydroxide aqueous solution to adjust the initial pH of the hydrogen peroxide solution to 6.2. Sodium hydroxide solution was periodically added throughout the reaction to maintain the pH at or above 5.0.

Comparative Example F

Epoxidation of Allyl Chloride Using Hydrogen Peroxide Solution Without Any Form of pH Adjustment or Control The procedure from Example 1 was repeated, but with the following changes. The pH of the hydrogen peroxide solution was not adjusted. Therefore, nothing was done to the hydrogen peroxide solution to adjust the pH.

Comparative Example G

Epoxidation of Allyl Chloride Using Hydrogen Peroxide Solution Without Any Form of pH Adjustment or Control and Catalyst Reuse The procedure from Comparative Example F was repeated, but with the following changes. Instead of using fresh TS-1 catalyst, the separated TS-1 catalyst from Comparative Example F was reused.

reaction mixture), "hydrogen peroxide utilization" is calculated as (the amount of hydrogen peroxide converted to epi)/(the amount of hydrogen peroxide that reacts during the epoxidation). The "selectivity" is the (amount of epi formed)/(amount of epi formed plus all by-products). The selectivity is illustrated in Table 1 as the amount of each by-product that is formed.

A factor in the epoxidation of the olefin is the pH of the reaction mixture. Therefore, when comparing the Examples with the Comparative Examples it is most meaningful to compare ones that are at approximately the same pH. Thus, Examples 1-4 are compared to Comparative Examples A-D and Examples 5-6 are compared to Comparative Examples

TABLE 1

| Example | Predetermined pH of the Hydrogen Peroxide Solution | Reaction Time (min) | Hydrogen Peroxide Conversion | Hydrogen Peroxide Utilization | CMP/epi | MCH/epi | Higher Molecular Weight By-products/epi |
|---|---|---|---|---|---|---|---|
| Example 1 | 5.7 | 60 | 99.40% | 93.40% | 1.00% | 0.40% | 0.44% |
| Example 2 | 5.0 | 60 | 99.80% | 93.90% | 0.80% | 0.30% | 0.12% |
| Example 3 | 5.2 | 60 | 99.40% | 88.70% | 0.90% | 0.30% | 0.21% |
| Example 4 | 5.2 | 60 | 97.30% | 90.90% | 1.00% | 0.50% | 0.15% |
| Example 5 | 4.5 | 60 | 98.70% | 89.90% | 0.80% | 0.30% | 0.17% |
| Example 6 | 4.6 | 60 | 99.50% | 92.60% | 0.80% | 0.30% | 0.17% |
| Example 7 | 5.5 | 60 | 99.70% | 86.10% | 0.80% | 0.30% | 0.17% |
| Example 8 | 5.6 | 90 | 99.40% | 84.20% | 1.50% | 0.60% | 0.29% |
| Example 9 | 5.6 | 60 | 99.70% | 75.20% | 0.90% | 0.30% | 0.17% |
| Example 10 | 5.4 | 90 | 99.50% | 74.90% | 1.80% | 0.60% | 0.35% |

TABLE 2

| Comparative Example | Predetermined pH of the Hydrogen Peroxide Solution | Reaction Time (min) | Hydrogen Peroxide Conversion | Hydrogen Peroxide Utilization | CMP/epi | MCH/epi | Higher Molecular Weight By-products/epi |
|---|---|---|---|---|---|---|---|
| Comparative Example A | 5.5 | 60 | 99.70% | 86.10% | 0.90% | 0.30% | 0.12% |
| Comparative Example B | 5.0 | 60 | 96.80% | 91.00% | 0.90% | 0.50% | 0.14% |
| Comparative Example C | 5.5 | 60 | 99.70% | 76.90% | 1.20% | 0.40% | 0.15% |
| Comparative Example D | 5.6 | 60 | 99.50% | 83.40% | 1.00% | 0.40% | 0.20% |
| Comparative Example E | 6.2 | 180 | 91.00% | 78.70% | 1.20% | 0.50% | 0.70% |

TABLE 3

| Comparative Example | pH of Reaction Mixture | Reaction Time (min) | Hydrogen Peroxide Conversion | Hydrogen Peroxide Utilization | CMP/epi | MCH/epi | Higher Molecular Weight By-products/epi |
|---|---|---|---|---|---|---|---|
| Comparative Example F | ~4 | 60 | 99.30% | 96.30% | 1.40% | 0.50% | 0.38% |
| Comparative Example G | ~4 | 120 | 99.00% | 93.60% | 2.70% | 1.00% | 0.57% |

Table 1 is a summary of the examples and Table 2 and Table 3 are a summary of the comparative examples. In the tables, "CMP" stands for 1-chloro, 3-methoxy, 2-propanol, "MCH" stands for 1-chloro-2,3-propanediaol (monochlorohydrin), and "epi" stands for epichlorohydrin.

The "hydrogen peroxide conversion" is calculated as (the total amount of hydrogen peroxide that reacts during the epoxidation)/(the amount of hydrogen peroxide added to the F-G. Also, it is understood by those skilled in the art that a few percent difference in the hydrogen peroxide utilization makes a significant difference in monetary savings as hydrogen peroxide is the most expensive reagent used in the epoxidation process.

Comparing Table 1 with Table 2 illustrates the benefits of using the supported base to adjust a hydrogen peroxide solution to a predetermined pH (Examples 1-4) versus using an ion exchange resin (Comparative Examples A-C) or a homogeneous ionic base (Comparative Example D). As can be seen in Table 1, Examples 1-4 maintain a high selectivity demonstrated by the lower amount of the by-products formed without decreasing the hydrogen peroxide conversion or hydrogen peroxide utilization. Comparative Examples A-D illustrated in Table 2, show that while the hydrogen peroxide conversion remains relativity high, the amount of the hydrogen peroxide converting to the epoxide is significantly decreased, which is shown as the hydrogen peroxide utilization.

The benefit of pH control (Example 5 and Example 6 in Table 1) versus no pH control (Comparative Example F and Comparative Example G in Table 3) is demonstrated by a significant decrease in the amount of CMP, MCH and higher molecular weight by-products formed during the epoxidation. The Comparative Examples F and G with no pH control demonstrate a reduced selectivity. The reduced selectivity for Comparative Examples F and G can be seen as the amounts of the CMP, MCH and higher molecular by-products are significantly increased as compared to Examples 5 and 6, which use pH control.

FIG. 1 illustrates the amount of epi formed over the course of the epoxidation of allyl chloride. FIG. 1 compares Examples 7-10 with Comparative Examples F and G. As seen in FIG. 1, adjusting the pH of the hydrogen peroxide solution with the supported base Amberlyst® A-21 (Example 7) or poly-4-vinylpyridine (Example 9) does not decrease the long-term effectiveness of the catalyst when the catalyst is reused (Example 8 and Example 10).

What is claimed:

1. A process for an epoxidation of an olefin, the process comprising:
    reacting the olefin, with the proviso that the olefin is not propylene, with a hydrogen peroxide solution in the presence of a titanium-silicalite catalyst and a solvent, wherein a pH of the hydrogen peroxide solution is adjusted by contacting the hydrogen peroxide solution with a supported base to remove acidic species from the hydrogen peroxide solution, wherein a selectivity of the epoxidation of the olefin is increased without decreasing a hydrogen peroxide utilization or a hydrogen peroxide conversion as compared to an epoxidation of an olefin without the supported base to adjust the pH of the hydrogen peroxide solution, and wherein the acidic species includes an ion and the supported base receives the ion but does not donate an ion to the hydrogen peroxide solution.

2. The process of claim 1, wherein reacting the olefin and the hydrogen peroxide solution is done in the presence of a co-solvent.

3. The process of claim 1, wherein the hydrogen peroxide solution includes a stabilizer, wherein the pH of the hydrogen peroxide solution is adjusted as the acidic species are removed from the stabilizer.

4. The process of claim 1, wherein the supported base has a predominantly neutral charge prior to adjusting the pH of the hydrogen peroxide solution.

5. The process of claim 1, wherein the supported base gains a positive charge in adjusting the pH of the hydrogen peroxide solution.

6. The process of claim 1, wherein the epoxidation reaction occurs at a constant reaction temperature.

7. The process of claim 1, wherein the olefin is allyl chloride and the epoxidation prepares epichlorohydrin.

8. The process of claim 1, wherein the pH is adjusted to within a range of from 1.0 to 9.0.

9. The process of claim 1, wherein the pH is adjusted to within a range of from 5.0 to 5.5.

* * * * *